US005939591A

United States Patent [19]

Birdwell et al.

[11] Patent Number: 5,939,591

[45] Date of Patent: Aug. 17, 1999

[54] APPARATUS FOR PRODUCING ALKYLENE GLYCOLS, ALKYLENE GLYOCOLS HAVING HIGHER PRIMARY HYDROXYL CONTENT, METHOD OF PRODUCING GLYCOLS HAVING HIGHER PRIMARY HYDROXYL CONTENT, METHOD OF PRODUCING ACRYLATE ESTERS

[75] Inventors: Jeffrey David Birdwell; Micheal L. Chappell; Philip Jay Carlberg; Frank Harold Murphy, all of Lake Jackson; Robert Page Shirtum, Freeport; Walter L. Wernli, Angleton, all of Tex.

[73] Assignee: The Dow Chemical Company, Midland, Mich.

[21] Appl. No.: 08/982,085

[22] Filed: Dec. 1, 1997

Related U.S. Application Data

[62] Division of application No. 08/433,705, May 3, 1995, Pat. No. 5,693,870, which is a continuation of application No. 08/141,398, Oct. 22, 1993, abandoned.

[51] Int. Cl.$^6$ .................................................... C07C 43/11

[52] U.S. Cl. .................................................... 568/623

[58] Field of Search .................................................... 568/623

[56] References Cited

U.S. PATENT DOCUMENTS

| | | |
|---|---|---|
| 1,976,677 | 10/1934 | Wittwer et al. . |
| 2,407,205 | 9/1946 | Wilkes . |
| 2,996,550 | 8/1961 | Simmons . |
| 3,436,425 | 4/1969 | Stein et al. . |
| 4,079,086 | 3/1978 | Satkowski et al. . |
| 4,453,023 | 6/1984 | McCain et al. . |
| 4,626,603 | 12/1986 | Siegmeier et al. . |
| 4,801,759 | 1/1989 | Siegmeier . |
| 4,988,797 | 1/1991 | Wardle et al. . |

*Primary Examiner*—Paul J. Killos
*Attorney, Agent, or Firm*—J. M. (Mark) Gilbreth; Robert W. Strozier; Gilbreth & Strozier, P.C.

[57] ABSTRACT

Disclosed is an apparatus and process for producing a tripropylene glycol in which alkylene oxide, water, an acid catalyst and a dipropylene glycol are contacted together under conditions suitable to form the tripropylene glycol. Water is present in the reaction mixture in the range of about 1 to about 50 weight percent of the reaction mixture. The ratio of water to alkylene oxide is less than about 9. The tripropylene glycol thus produced exhibits a higher primary hydroxyl group content generally exceeding 36 percent. Such tripropylene glycols find utility in the production of acrylics. Also disclosed is a process for making esters from such glycols.

4 Claims, 2 Drawing Sheets

APPARATUS FOR PRODUCING ALKYLENE GLYCOLS, ALKYLENE GLYOCOLS HAVING HIGHER PRIMARY HYDROXYL CONTENT, METHOD OF PRODUCING GLYCOLS HAVING HIGHER PRIMARY HYDROXYL CONTENT, METHOD OF PRODUCING ACRYLATE ESTERS

This application is a division of Application Ser. No. 08/433,705, filed on May 3, 1995 U.S. Pat. No. 5,693,870, which is a continuation of Application Ser. No. 08/141,398, filed on Oct. 22, 1993, now abandoned.

BACKGROUND OF THE INVENTION

1. Field of the Invention

The present invention relates to alcohols, to apparatus for producing alcohols, to a method of producing alcohols, and to a method of producing esters from alcohols. In another aspect, the present invention relates to alkylene glycols, to apparatus for producing such glycols, to a method of producing such glycols, and to a method of producing esters from such glycols. In yet another aspect, the present invention relates to alkylene glycols having an increased primary hydroxyl content, to apparatus for producing such glycols which include one or more continuous stirred tank reactors in series feeding a plug flow reactor, to a method of producing such glycols from a reaction mixture of water, lower order alkylene glycols, alkylene oxide and acid, and to a method of producing acrylate esters from such glycols.

2. Description of the Related Art

Monoalkylene glycols are generally produced by the hydrolysis of the alkylene oxide at large excess of water, generally on the order of 15 to 40 moles water to mole of alkylene oxide, with water generally comprising 85 weight percent of the reaction mixture. See, Kirk-Othmer Encyclopedia of Chemical Technology, 3rd. ed. (hereinafter "Kirk-Othmer"), Vol. 19 at 246–274 and 250.

Higher order alkylene glycols are generally produced either as by-products in the hydrolysis of monoalkylene oxides or as by-products in the production of lower order alkylene glycols, or are produced directly through one or more additions of an alkylene oxide with a lower order alkylene glycol.

For example, in the production of monopropylene glycol through the hydrolysis of propylene oxide at a large excess of water of 15 moles water/mole propylene oxide, the product mix is generally 85 percent propylene glycol, 13 percent dipropylene glycol, and 1.5 percent tripropylene glycol and higher adducts. See, Kirk-Othmer, Vol. 11 at 933–956 and 952.

Tripropylene glycol can also be obtained directly by the addition of propylene oxide to dipropylene glycol, generally in a catalyzed process. Since water is a competitor with the dipropylene glycol for the propylene oxide, its presence in the reaction mixture is to be avoided.

In the production of tripropylene glycol both primary and secondary hydroxyl groups are obtained. It is understood that the produced glycols will have either two primary hydroxyl groups, two secondary hydroxyl groups or one of each. As used herein the primary hydroxyl content is a percentage of the hydroxyl groups that are primary.

The primary hydroxyl group content obtained in the prior art propylene glycol processes is generally in the range of about 15 to about 36 percent. However, there is a need in the art for alkylene glycols having a higher primary hydroxyl group content.

There is also a need in the art for a process useful in providing alcohols, especially higher order alkylene glycols, having higher primary hydroxyl group content.

There is also a need in the art for an apparatus useful in providing alcohols, especially higher order alkylene glycols, having higher primary hydroxyl group content.

There is also a need in the art for a process useful in providing esters from alcohols and organic acids, the process having increased alcohol conversion and/or an increased reaction rate.

SUMMARY OF THE INVENTION

It is therefore one object of the present invention to provide for alkylene glycols having a higher primary hydroxyl group content.

It is therefore another object of the present invention to provide a process useful in producing alcohols, especially higher order alkylene glycols, having higher primary hydroxyl group content.

It is yet another object of the present invention to provide an apparatus useful in producing alcohols, especially higher order alkylene glycols, having higher primary hydroxyl group content.

It is even another object of the present invention to provide a process useful in producing esters from alcohols and organic acids, the process having increased alcohol conversion and/or an increased reaction rate.

Other objects of the present invention will become evident to those of skill in the art upon review of the foregoing disclosure of the invention.

As discussed above, it is known in the prior art that dipropylene glycol and propylene oxide react to form tripropylene glycol. It is also known in the prior art that water and alkylene oxide react to form monopropylene glycol, with the water present at 15 plus mole excess and comprising 85 percent of the reaction mixture.

From these reactions, the prior art teaches that when forming tripropylene glycol by the reaction of a dipropylene glycol and propylene oxide, any water present in the reaction mixture would compete with the dipropylene glycol for the propylene oxide resulting in a reduced tripropylene glycol production rate.

Surprisingly, the presence of water in the reaction mixture, at low water to alkylene oxide ratios and/or at a low concentration, actually enhances the production rate of the desired tripropylene glycol, and enhances the primary hydroxyl content of the final end product.

Equally unexpectedly, was the novel reactor design, which included one continuous stirred tank reactor ("CSTR"), or several in series, which allowed for the production of higher order alkylene glycols having a higher primary hydroxyl content, under increased reaction rates. Also unexpected was the improved results achieved with the combination of utilizing a plug flow reactor in combination with one or more CSTRs.

Also surprising, was an alternate semi-batch reactor design in which alkylene oxide and the acid were over time slowly added to the reaction mixture of water, and the other order alkylene glycols.

According to one embodiment of the present invention there is provided a process for producing an Nth order alkylene glycol. The method generally includes the step of contacting together in a reaction mixture alkylene oxide, water, an acid catalyst and one or more lower order alkylene glycols under conditions suitable to form the Nth order alkylene glycol. As compared to prior art methods, water is present in small amounts and comprises in the range of about 1 to about 60 weight percent of the reaction mixture. The mole ratio of water to alkylene oxide is less than about 9.

As a specific example of this embodiment, there is provided a process for producing a tripropylene glycol in which alkylene oxide, water, an acid catalyst and dipropylene glycol are contacted together under conditions suitable to form the tripropylene glycol.

According to another embodiment of the present invention there are provided 2nd and higher order alkylene glycols having an increased primary hydroxyl group content as compared to such glycols achieved by prior art methods. In a specific example of this embodiment, there is provided a tripropylene glycol composition having a higher primary hydroxyl group content than the prior art content of about 15 to about 36 percent. The inventive tripropylene glycol composition of the present invention generally has a primary hydroxyl content greater than 36 percent.

According to yet another embodiment of the present invention there is provided an apparatus for producing higher order alkylene glycols. The apparatus generally includes one or more continuous stirred tank reactors ("CSTR") in series feeding a plug flow reactor. The CSTR will receive a mixture of water, alkylene oxide, and lower order alkylene glycols, generally in a combined stream. Acid is slowly added to the reactor, through a heat exchange loop. The reactor contents are maintained in a stirred state by return of material from the heat exchange loop which is injected into the reactor at high velocity through nozzles. As the reaction mixture exits the CSTR with about 90 to 99 percent of the alkylene oxide converted, the plug flow reactor allows for substantially complete conversion of the alkylene oxide.

According to still yet another embodiment of the present invention there is provided a process for producing higher order alkylene glycols in which water, alkylene oxide, and lower order alkylene glycols are continuously introduced into a reactor. Inside the reactor, the reaction mixture is subjected to continuous heating and vigorous stirring. Simultaneously, product is withdrawn from the reactor and fed to a second reactor to undergo plug flow through the reactor.

According to even yet another embodiment of the present there is provided a semi-batch process for producing higher order alkylene glycols in which water, and lower order alkylene glycols are first batched into a reactor to form a reaction mixture. Subsequently, alkylene oxide and acid are added to the reaction mixture over the course of the process.

According to even still yet another embodiment of the present invention there is provided a process for producing esters. This method generally includes as a first step contacting together in a reaction mixture alkylene oxide, water, an acid catalyst and an (N−1)th order alkylene glycol under conditions suitable to form a Nth order alkylene glycol, under conditions as described above. The second step of this method includes contacting the Nth order alkylene glycol of the first step with a carboxylic acid in the presence of an acid catalyst to form an ester.

While the present invention is illustrated herein specifically for the reaction of an alkylene oxide with glycol, it is understood that the teachings of the present invention are believed to be equally applicable to reactions of alkylene oxide with alcohols in general, including mono-, di-, tri- and polyhydric alcohols. Therefore, such reactions are within the scope of the disclosure of the present invention.

DETAILED DESCRIPTION OF THE INVENTION

Figure 1:
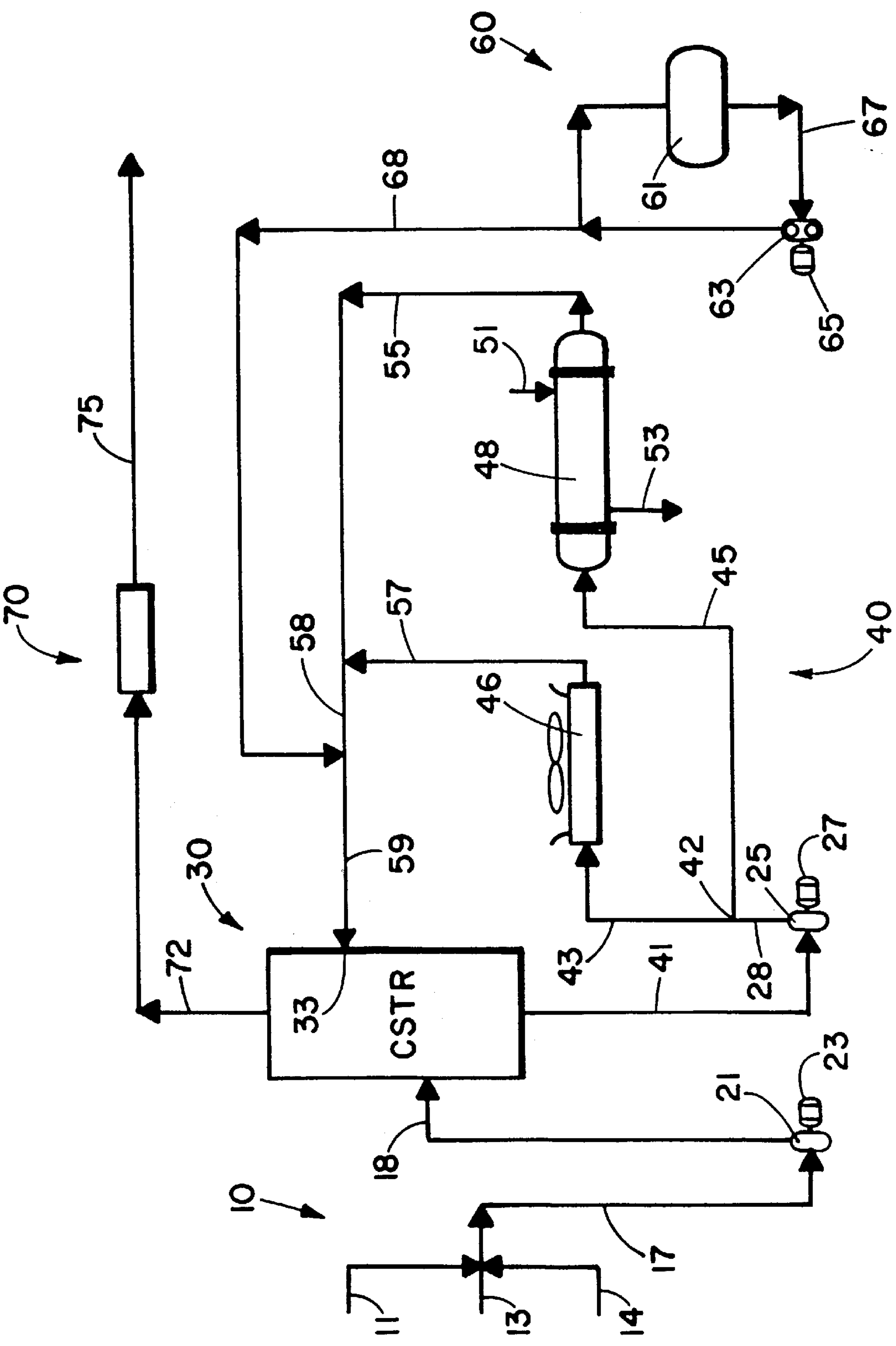
FIG. 1 is a schematic of one embodiment of the continuous stirred tank reactor system of the present invention, showing feed streams 10, reactor 30, heating and cooling loop 40, acid addition system 60 and plug flow reactor 70.

In the practice of the present invention a higher order alkylene glycol adduct is generally produced from a reaction mixture that includes a small amount of water, alkylene oxide, an acid catalyst, and a lower order alkylene glycol adduct. Surprisingly, the presence of the small amount of water in the reaction mixture increases the production rate of the higher order alkylene glycol. Additionally, in the practice of the present invention higher primary hydroxyl content is obtained in the higher order alkylene oxide product.

As used herein, the "order" of an alkylene glycol adduct refers to the number of alkylene units in the alkylene glycol addition product. For example, a monoalkylene glycol is first order, dialkylene glycol is second order, trialkylene glycol is third order, tetraalkylene glycol is fourth order, etc.

It is most unexpected that the presence of water in the reaction mixture, at low water to alkylene oxide ratios and/or at a low concentration, would actually enhance the production rate of the desired tripropylene glycol. Additionally, in the practice of the present invention, higher primary hydroxyl group content is obtained in the final end product as compared to prior art methods.

At the very least, water is generally present in the reaction mixture in an amount suitable to promote increased rate of formation of the desired higher order alkylene glycol adduct. The concentration or mole ratio of water utilized in the present invention must be less than that which would unduly inhibit the production of the desired higher order alkylene glycol adduct.

Generally, water is present in the reaction mixture in a concentration in the range of about 1 to about 60 weight percent based on the total weight of the reaction mixture. Preferably, the concentration of water in the reaction mixture is in the range of about 10 to about 50 weight percent, and more preferably in the range of about 10 to about 35 weight percent. Even more preferably, the concentration of water in the reaction mixture is in the range of about 15 to about 30 weight percent.

In the present invention, the mole ratio of water to alkylene oxide is generally less than about 14:1. Preferably, the mole ratio of water to alkylene oxide in the reaction mixture is in the range of about 12:1 to about 1:1, more preferably in the range of about 10:1 to about 2:1, and most preferably in the range of about 8:1 to about 2:1.

The alkylene oxide utilized in the present invention is generally selected to provide the desired higher order alkylene glycol adduct. For example, where the desired higher order alkylene glycol adduct is tripropylene glycol, propylene oxide is utilized. Where the desired higher order alkylene glycol adduct is tributylene glycol, butylene oxide is utilized. The alkylene oxide of the present invention is generally of the empirical formula:

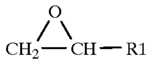

wherein R1 is a C1 or higher order alkyl or substituted alkyl. Preferably, R1 is a C1 to C3 alkyl or substituted alkyl. More preferably, R1 is a C1 to C2 alkyl or substituted alkyl, and most preferably, R1 is a C1 alkyl or substituted alkyl.

Exemplary examples of the alkylene oxide utilized in the present invention include propylene oxide and butylene oxide.

Most preferably, the alkylene oxide of the present invention is generally of the empirical formula:

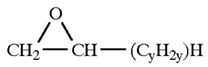

wherein y is at least one, preferably y is 1 to 3, and most preferably y is 1 or 2.

In the practice of the present invention the concentration of free alkylene oxide in the reaction mixture must generally be minimized to avoid a runaway reaction, and/or to avoid deactivation of the catalyst. Generally, the concentration of the alkylene oxide in the reaction mixture is in the range of about 0.01 to about 20 weight percent. Preferably, the concentration of the alkylene oxide in the reaction mixture is in the range of about 0.1 to about 8 weight percent, and most preferably in the range of about 0.1 to about 6 weight percent.

The acid catalyst utilized in the present invention is generally selected to catalyze the reaction mixture reactants in the formation of the desired higher order alkylene glycol. Acids suitable for use in the present invention are any non-oxidizing strong acid, having a counter ion that is a good leaving group and/or a poor nucleophile.

Classes of acids suitable for use in the present invention include those having sulfuric or phosphoric functional groups. Examples of such acids include: sulfuric acid; substituted or unsubstituted alkyl-, aryl- or alkyl/aryl-sulfonic acids; phosphoric acid; substituted or unsubstituted alkyl-, aryl- or alkyl/aryl-phosphoric acids and sulfonic ion exchange resins. Preferably, the acid utilized in the present invention is selected from the group consisting of sulfuric acid, phosphoric acid, trifluoromethane sulfonic acid and para-toluene sulfonic acid.

The desired higher order alkylene glycol adduct produced by the process of the present invention is generally of the empirical formula:

$$HO\ R2O\text{-})_{(N-1)}(CH(R1)CH_2)OH$$

wherein N is the order of the alkylene glycol and is at least 2, R1 is as described above, and each R2 is the same as R1 or each R2 is independently selected from among alkyls or substituted alkyls with 3 or more carbon atoms. Preferably, each R2 is independently selected from among alkyls or substituted alkyls having 3 to 5 carbon atoms. Most preferably, N is 2 or 3 and each R2 is independently selected from among alkyls or substituted alkyls having 3 to 4 carbon atoms. Even more preferably, N is 3 and each R2 is independently selected from among propyl or substituted propyls. Still even more preferably, N is three and each R2 is propyl.

Preferable desired higher order alkylene glycol adducts produced by the process of the present invention are of the empirical formula:

$$HO(C_xH_{2x}O\text{-})_{(N-1)}(CH(C_yH_{(2y+1)})CH_2)OH$$

wherein N is the order of the alkylene glycol and is at least 2, and x is greater than 3 and y is at least 1. Preferably, N is 2 to 4, y is 1 or 2, and x is 3 or 4. Most preferably, N is 3, y is 1, and x is 3.

Examples of higher order alkylene glycols which may be produced in the present invention include dipropylene glycol, tripropylene glycol, tetrapropylene glycol, dibutylene glycol, tributylene glycol and tetrabutylene glycol.

It is to be understood that in the production of an Nth order alkylene glycol adduct, the reaction mixture may include any one of or combination of 1st to (N−1)th order alkylene glycols. These lower order alkylene glycols may be added to the reaction mixture or they may be made in-situ.

The lower order alkylene glycol adduct utilized in the present invention is generally selected to allow production of the desired higher order alkylene glycol adduct. Thus, the lower order alkylene glycol adduct utilized in the reaction mixture will generally have the empirical formula:

$$HO(R2O\text{-})_MH$$

wherein M may range from 1 to N−1, where N is at least 2 and N is the order of the desired higher order alkylene glycol, and wherein R2 is as described above.

Preferable lower order alkylene glycol adducts present in the reaction mixture are of the empirical formula:

$$HO(C_xH_{2x}O\text{-})_MH$$

wherein M and x are as described above.

For example, where the higher order alkylene glycol to be produced is tripropylene glycol, the lower order alkylene glycols which may be present in the reaction mixture include monopropylene glycol and dipropylene glycol.

The process of the present invention may be carried out in any suitable reactor that will allow production of the desired higher order alkylene glycol adduct from a reaction mixture that includes a lower order alkylene glycol adduct, alkylene oxide, water and an acid catalyst.

An example of a suitable reactor system includes a semi-batch reactor process in which the water, lower order alkylene glycol, and some of the acid catalyst is first charged to the reactor, followed by slow addition of the alkylene oxide and periodic charging of the remainder of the acid catalyst. It is generally necessary to maintain a low level of alkylene oxide in the reaction mixture. At the very least, acid catalyst is added at a rate necessary to avoid accumulation of alkylene oxide. Higher acid levels tend to cause quicker catalyst deactivation, and may pose corrosivity problems in the reactor and attendant equipment. Thus, at the upper limit, acid catalyst is added at a low enough rate to avoid rapid catalyst deactivation and to avoid corrosivity problems.

The reaction mixture in the semi-batch reactor is generally subjected to mixing suitable to maintain the alkylene oxide in intimate contact with the other reactants. Any of the mixing techniques known to those of skill in the art may be utilized, such as with an internal impeller, or by recirculating the reaction mixture and reinjecting it back into the reactor through nozzles. The alkylene oxide will generally be in gaseous form, with the remainder of the reactants in liquid form. Thus, to improve the contacting of the alkylene oxide with the other reactants, the reactor is generally operated at or near liquid full to minimize the vapor space. Additionally, the alkylene oxide may be sparged into the bottom of the reactor.

The semi-batch reactor is generally operated for a reaction time suitable to obtain the desired product and desired reactant conversion. Generally, such semi-batch reaction times are on the order of about 5 minutes to about 100 hours. Preferably, semi-batch reaction times are in the range of about 15 minutes to about 50 hours, more preferably in the range of about 30 minutes to about 30 hours, and most preferably in the range of about 5 hours to about 30 hours.

Another reactor system suitable for use in the present invention includes a continuous stirred tank reactor ("CSTR") in which the alkylene oxide, water, lower order alkylene glycol and acid are continuously fed to the reactor. The reactants may be introduced into the CSTR either premixed or through separate conduits. Where there is a concern that the reaction will be catalyzed in the feed stream, the acid is introduced to the CSTR separately from the other reactants to avoid a runaway reaction in the feed stream.

In the design of the CSTR system, it is also preferable to utilize some of the heat produced in the CSTR to preheat the incoming alkylene oxide, glycol and water feed mixture to increase the alkylene oxide conversion.

In a CSTR system, the steady state concentration of the alkene oxide will generally be less than that in utilized in a batch process. In general, the steady state concentration of the alkylene oxide in the CSTR is generally maintained at a very low level on the order of about 0.1 to about 6 weight percent based on the weight of the reactor mixture. A product stream is continuously removed from the reactor. As the conversion of the alkylene oxide is generally in the range of about 90 to about 99 percent, further conversion in a subsequent reactor is optionally undertaken as desired. If subsequent conversion is desired, one suitable option is to feed the product stream from the CSTR to a plug flow reactor where the remainder of the alkylene oxide will be converted. Examples of suitable plug flow reactors useful in the present invention include a tubular reactor or a tank having plug flow enhancing elements such as baffles, structural packing or random packing.

The reaction mixture in the CSTR is generally subjected to mixing adequate to maintain the alkylene oxide in intimate contact with the other reactants. Any of the mixing techniques known to those of skill in the art may be utilized, such as with an internal impeller, or by recirculating the reaction mixture and reinjecting it back into the CSTR through nozzles. As with the semi-batch reactor described above, it is preferable to operate the CSTR at or near liquid full.

Residence times in the CSTR are generally suitable to obtain the desired higher order alkylene glycol product and obtain the desired reactant conversion. Generally, CSTR residence times are in the range of about 1 second to about 12 hours. Preferable CSTR residence times are in the range of about 1 minute to about 6 hours, and most preferably in the range of about 10 minutes to about 2 hours.

Referring now to FIG. 1 there is illustrated in schematic form one embodiment of the CSTR system of the present invention, showing feed streams 10, CSTR 30, heating and cooling loop 40, acid addition system 60 and plug flow reactor 70.

Water feed stream 11, alkylene oxide feed stream 13 (propylene oxide in the embodiment shown) and dialkylene glycol feed stream 14 (dipropylene glycol in the embodiment shown) form reactant feed stream 17 which is pumped via pump 21 and motor 23 via stream 18 to CSTR reactor 30. Acid is provided from acid addition tank 61 from acid circulation loop 67 via acid slip stream 68 and reinjection stream 59. Acid circulation is maintained by acid circulation pump 63 powered by motor 65.

Heating and cooling of the reaction mixture is provided by heating and cooling loop 40 which includes cooler 46, heater 48 and heating and cooling loop pump 25 with motor 27. In the embodiment shown, cooler 46 is an air cooler, and heater 48 is a steam heater with steam inlet line 51 and condensate return line 53. Stream 41 circulates the reaction mixture to pump 25. Pump outlet stream 28 is split at valve 42 to cooler 46 via steam 43 or to heater 48 via stream 45. Cooler return line 57 joins with heater return line 55 to form stream 58, which is joined by acid slip stream 68 to form reinjection stream 59. Stream 59 is reinjected into CSTR 30 via nozzles 33 which provide adequate mixing of the reaction mixture. Reaction mixture is continuously removed from CSTR 30 and fed to plug flow reactor 70 via line 72. Product leaves plug flow reactor 70 via line 75.

As a non-limiting example of the reactor design a tank with straight vertical sides, a cylinder, and rounded top and bottom may be utilized. The reactor has height:diameter ratio on the order of 1. The feed will enter the reactor just below the straight side to head weld and the desired product will flow out of the top of the CSTR to the plug flow reactor. A recycle loop going to the heat exchanger will exit from the center bottom of the reactor and return through one or more jets located on the head just below the straight side to head weld at an angle of about 40° from the vertical. At startup the CSTR is filled and feed is heated in a heat exchange loop, with the same loop used for cooling when necessary. Acid addition will also take place in the heat exchange loop. Some of the product stream from the CSTR will be routed to the plug flow reactor for completion of the alkylene oxide conversion. Entry into the plug flow reactor will generally not be at the beginning of the plug flow reactor, but will be at a suitable point generally half way through the plug flow reactor. The ratio of feed to the CSTR to feed to the plug flow reactor is generally less than about ½, e.g. ⅓.

The reaction temperature and reaction pressure of the present invention are generally suitable to allow production of the desired higher order alkylene glycol adduct from a reaction mixture that includes a lower order alkylene glycol adduct, alkylene oxide, water and an acid catalyst. In the present invention, the reaction temperature and reaction pressure are very much a function of the water concentration and the type of catalyst utilized.

In the present invention, the reaction rate generally increases with increasing temperature. Therefore, it is generally desirable to practice the present invention at the maximum convenient temperature below the temperature at which significant decomposition of the reaction mixture components or product takes place. It is also desirable that the reaction temperature be selected to maintain the water and alkylene glycol in the liquid phase. Thus, generally the reaction temperature is greater than the water/glycol mixture freezing point at the reaction pressure and less than the water/glycol mixture boiling point at the reaction pressure.

Generally, depending upon the catalyst utilized, suitable reaction temperatures are in the range of about −60° C. to about 300° C. More commonly, the reaction temperature is in the range of about 20° C. to about 180° C. It is understood that preferred reaction temperatures will depend upon the specific type of catalyst utilized, as reaction temperature is also generally selected to provide an environment in which the acid catalyst will not be subject to undue degradation.

For example, with perfluorosulfuric acid polymers, the preferred reaction temperature is in the range of about 20° C. to about 90° C. With phosphoric acid, the preferred reaction temperature is in the range of about 100° C. to about 200° C.

The reaction pressure for the present invention should be selected so that the water and glycol in the reaction mixture will generally be in liquid form even when higher reaction temperatures are utilized. Suitable pressures will be in the range of about 1 to about 100 atmospheres, preferably in the range of about 1 to about 20 atmospheres.

The higher order alkylene glycol product obtained with the process of the present invention comprises glycols having primary hydroxyl group, secondary hydroxyl groups or both. One advantage of the present invention is that second order and higher alkylene glycols can be obtained which have higher primary hydroxyl content than that obtained with the prior art processes.

The primary hydroxyl group content of the higher order alkylene glycol produced in the present invention generally exceeds 36 percent. Preferably, the primary hydroxyl group content of the higher order alkylene glycol exceeds 40 percent, more preferably exceeds 44 percent and most preferably exceeds 48 percent.

Once the higher order alkylene glycol product is recovered, the various components of the reaction mixture are separated by techniques well known to those of skill in the art. Generally, distillation is used to separate the various components of the reaction mixture.

The higher order alkylene glycol products of the present invention having a higher primary hydroxyl content find utility in a wide range of applications, including the production of esters.

In contacting the desired higher alkylene glycol of the present invention with an acid to made an ester, the inventors believe that the higher primary hydroxyl content will result in less unreacted glycols in the product mixture which is economically desirable, and also technically desirable as the unreacted glycols are difficult to separate from the ester product. Additionally the inventors believe that the higher primary hydroxyl content will speed the reaction rate and will thus avoid many of the problems associated with long reaction times, i.e., detrimental heat history, coloring and an increased viscosity.

In the production of esters, the higher order alkylene glycol is contacted with 10 to 20 mole percent excess of a carboxylic acid in the presence of an acid catalyst to form the ester. Suitable acid catalysts generally include Lewis or Bronsted acids such as paratoluene sulfonic acid or dibutyl tin oxide. It is generally necessary to remove water from the reaction mixture to drive the reaction, in many instances with the aid of an azeotroping agent, such as xylene or toluene.

The higher order alkylene glycol products of the present invention having a higher primary hydroxyl content are especially useful in the production of acrylate esters in which acrylic acid and the glycol are generally reacted as described above.

EXAMPLES

Example 1

This example is for comparative purposes showing the reaction of propylene oxide and dipropylene glycol in the absence of water without catalyst (batch).

Recipe:

41.51 grams of propylene oxide (“PO”)

0.0 grams of water 1860.0 grams of dipropylene glycol (“DPG”)

Conditions:

125°

250 rpm 85 psig 1 sample per hour

The reactor was charged liquid full with DPG and allowed to reach 124° C., and an additional 44 mls of reaction mixture was removed from the reactor vessel to insure a complete PO charge. The PO charge was rapidly injected into the highly agitated reaction mixture. Sample #0 was removed after 1 minute of elapsed reaction time, the agitator speed was lowered to 250 rpm, and the sample analyzed. Thereafter samples of the reaction mixture were removed and analyzed every hour for six hours.

PO conversion was determined and found to be 11.2%. PO conversion, even in the liquid filled vessel, was much lower than expected. The data were used to determine the kinetic parameters for the reactions in the absence of water, since the available literature data for the parameters of the uncatalyzed reactions of PO, PG, and DPG, were obtained in solutions containing a large excess of water.

Example 2

This example shows the effect of a small amount of water on the reaction of propylene oxide and dipropylene glycol without catalyst (batch).

Recipe:

40.34 grams of PO 18.47 grams of water 1828.5 grams of DPG

Conditions:

125° C.

250 rpm 100 psig 1 sample per hour

The reactor was filled with the recipe mixture of water (1%) and DPG and heated to 125° C. The PO charge was injected into the reactor, the reaction mixture agitated for 2 minutes, and sample #0 was removed and analyzed. Additional samples were removed, and analyzed every hour for 3.5 hours. The data from the samples indicated a PO conversion of 10.3%, compared to 8.3% PO conversion at 3.5 hours in Example 1. The rate of reaction increased by about 25% using a low concentration of water versus no addition of water.

Example 3

This example shows the effect of using a higher water concentration, to better define the effect of water in the hydrolysis and coupling reactions.

Recipe:

40.4 grams of PO 96.55 grams of water 1834.5 grams of DPG

Conditions:

125° C.

250 rpm 100 psig variable sample frequency

The recipe quantities of water (5%) and DPG were mixed, poured into the reactor, and heated to reaction temperature. When the temperature stabilized 125° C., and the agitator stabilized at 750 rpm, the PO charge was injected into the reaction mixture. Sample #0 was removed after two minutes of reaction after which time the agitator speed reduced to 250 rpm. Subsequent samples of the reaction mixture, were obtained at approximately 30 minute intervals for 1.3 hours and then every hour for an additional 3 hours, and analyzed. PO conversion was determined to be 15.1% after 4.3 hours reaction time. When compared with a PO conversion of 10.2% for Example 1, after the same elapsed reaction time, the data shows that the conversion rate increased by about 50%. Another noticeable effect of the increased water content was the increased quantity of propylene glycol (PG) in the reaction product The PG increased from 0.02%, in Example 1, to 0.2% in this example.

As this experiment shows, the effect to water on the rate of reaction, at 5% water, is not very great.

Example 5

This example was performed in an autoclave reactor using a base catalyst as is well known in the prior art.

Recipe:

44.74 grams of PO 16.57 grams of water 1837.9 grams of DPG 1.6 grams of 50% NaOH solution Conditions:

125° C.

250 rpm 100 psig variable sample frequency

The precatalyzed reaction mixture containing the caustic was heated to 125° C. and the PO charge was injected into the highly agitated reaction solution. Sample #0 was obtained from the reactor through the sample cooling coil at the bottom of the reactor. A single drop of 25% sodium dihydrogen phosphate (75% water) solution was added and the sample was vigorously shaken to neutralize any NaOH in the sample. The samples, obtained every 10 minutes, were neutralized, filtered, and analyzed.

The data showed that the caustic catalyzed reaction had produced a final PO conversion of 86.5%. The reaction solution contained 0.08% PG, 7.3% TPG, and 0.1% TEPG. The yield to TPG versus PO conversion was exceptional when compared to the previous reactions, but the data on the final product sample indicated that a large fraction of the mass of the TPG product was the undesirable secondary hydroxyl isomers.

Reactions using phosphoric acid as the reaction catalyst were studied as the first choice to develop a homogeneous acid catalyzed process to produce TPG commercially.

Example 5

This example illustrates the use of phosphoric acid as the reaction catalyst.

Recipe:

42.29 grams of PO 100.0 grams of water 1850.0 grams of DPG 0.96 grams of 85% H3PO4 acid (426 ppm)

Conditions:

125° C.

250 rpm 100 psig 6 samples per hour

The water content of the reaction mixture was increased to 5% water, as other experiments indicated that at 1% water the catalyst was deactivating in about 30 minutes. The catalyst concentration was also increased to 426 ppm to aid in achieving a higher PO conversion and faster reaction rate.

The reaction mixture was sampled eight times in 1 hour and 45 minutes of reaction time. The analysis of the samples showed a higher PO conversion had been achieved, and more TPG was produced. PO conversion was 67.7%, and the product mixture contained 3.5% TPG. The mixture also contained 0.7% propylene glycol (PG).

The catalyst still lost activity after 30 minutes. The catalyst extinction time remained essentially the same, even with the addition of more water to and an additional quantity of catalyst.

Example 6

This experiment shows the effect of adding portions of the acid catalyst during the reaction.

Recipe:

47.70 grams of PO 100.0 grams of water 1801.0 grams of DPG 0.48 grams of 85% H3PO4 acid (200 ppm)+four 200 ppm additions(con-adds)

Staged-addition recipe:

8 mls DPG 2 mls water 0.47 grams of 85% H3PO4 in the con-add mixture

Conditions:

125° C.

250 rpm 250 psig sample frequency was variable

The reaction mixture was heated to 125° C., agitation increased to 750 rpm, sample #0 was removed, and the PO charge injected into the vigorously agitated solution. After two minutes, reactor agitation was reduced to 250 rpm, and sample #1 obtained; at ten minutes, sample #2 was obtained; at 15 minutes staged-addition #1 was injected into the reaction mixture. This was accomplished by the pressurized injection of the staged-addition mixture, using the PO injection cylinder. Two minutes after the staged-addition, sample #3 was obtained; 7 minutes later sample #4 was obtained; at twenty five minutes of elapsed reaction time, staged-addition #2 was injected, and the sampling cycle repeated. The cycle was repeated until a total concentration of 1000 ppm H3PO4 catalyst was achieved in the reactor solution. Eleven reaction samples and an original feed mixture sample were obtained, analyzed.

The data showed the PO conversion was 96.5%, and the final reactor mixture composition was 1.0% PG, 5.3% TPG, 0.2% TEPG, 0.09% of residual unreacted PO, with the balance comprising DPG and water. The reaction was accomplished in 1.33 hours. The slope of the PO conversion line was smooth until the PO concentration in the reaction mix was less than 0.5%. The slope of the conversion curve flattened out as the PO concentration decreased. The curve for the appearance of TPG matched the rate of disappearance of PO.

A comparison of the data from Example 5 and this Example 6, showed that the rate at which TPG appeared in the two reactions to be essentially the same, even though Example 5 utilized 426 ppm of H3PO4 versus the 200 ppm, staged-addition of the H3PO4 catalyst utilized in Example 6.

One major difference noted is that the final composition from Example 6 contained 1.9% more TPG than the composition from Example 5. The pulsed con-adds kept an active quantity of catalyst in the reaction mix at all times, thus achieving a higher PO conversion and a higher yield to TPG.

Example 7

This example compares how a total of 400 ppm, in 40 ppm staged-additions of H3PO4, perform versus the single catalyst addition to the reaction of Example 5.

Recipe:

45.25 grams of PO 100.0 grams of water 1814.0 grams of DPG 0.08 grams of 85% H3PO4 acid solution (40 ppm)

Staged-addition recipe:

18 mls DPG 2 mls water 0.08 grams of 85% H3PO4 in the staged-addition mixture.

Conditions:

125° C.

250 rpm 250 psig sample frequency was variable

The reaction mix was heated to 125° C. and the PO charge injected into the reaction solution. The reaction mixture was sampled on 3 minute intervals, and injections of the 40 ppm H3PO4 staged-addition mixture were made on ten minute intervals. This sample and staged-addition cycle was maintained for 1 hour and fifteen minutes reaction time. The reaction was continued for an additional hour after the final 40 ppm H3PO4 staged-addition, and samples obtained on 30 minute intervals.

A small exotherm, about 1° C., was observed after each staged-addition of catalyst to the reaction mixture.

The data shows a smooth, continuous PO conversion profile throughout the reaction, and the expected loss of catalytic activity after the final H3PO4 staged-addition.

PO conversion was 79.8%, and the final reaction mix sample contained 3.6% TPG, 0.8% PG, 0.1% TEPG with the balance comprising DPG and water. The data for this Example 7 shows that the staged-addition PO increases the conversion rate of propylene oxide as compared to the single PO addition of Example 5. The slope of the PO conversion curve was much steeper in Example 5, due to the initially higher concentration of H3PO4 catalyst, even though the two reactions achieved approximately the same final concentration of TPG; 3.4% for Example 5 and 3.6% for Example 7.

Example 8

This example studies the effect of using a perfluorosulfonic acid polymer on a solid support of sintered ⅛" alumina spheres.

Recipe:

45.25 grams of PO 100.0 grams of water 1814.0 grams of DPG 100.0 grams of supported perfluorosulfonic acid polymer Conditions:

125° C.

300 rpm 250 psig sample frequency was variable

The PO charge was injected into the hot, agitated, reaction mixture. The reaction temperature increased from 125° C. to 133° C. in about 5 seconds. Total reaction time was 2.6 hours.

The data showed the PO conversion to be 93.8% in the first 2 minutes of the reaction, and full PO conversion was achieved at 5 minutes of elapsed reaction. The reaction produced 5.9% TPG, 0.4% PG, and 0.5% of tetrapropylene glycol ("TEPG") and pentapropylene glycol ("PEPG") with the balance comprising water and DPG.

The exotherm noted during the early portion of the reaction indicates that a significant reduction in the reactor temperature can be made with this catalyst and the reaction would still proceed to completion in a reasonable time.

The primary hydroxyl group content of the TPG produced was 29.78 percent.

Example 9

Recipe:

43.3 grams of PO 20.0 grams of water 1838.0 grams of DPG 100.0 grams of supported perfluorosulfonic acid polymer Conditions:

65° C.

300 rpm 250 psig sample frequency was variable

This Example No. 9 was performed using the same catalyst used in Example No. 8. The catalyst was water washed to remove any residual organics, left over from Example No. 8. The reactor was charged with the same recipe mixture as in Example No. 8, and the PO charge injected. A 1° C. exotherm was observed for 2 about minutes.

PO conversion was 50% after about 10 minutes of reaction. The final sample of the reaction mixture showed that PO conversion was 94.6%. The reaction product also contained 5.2% of TPG, 0.2% MPG, 0.5% TEPG, and 0.5% PEPG with DPG and water comprising the balance. The supported perfluorosulfonic acid catalyst was very active compared to the previously studied acid catalysts.

The primary hydroxyl group content of the TPG produced was 31.28 percent.

Example 10

This example, using a supported perfluorosulfonic acid polymer catalyst, was performed in an attempt to reduce the formation of undesirable byproducts, by reducing the reaction temperature.

Recipe:

46.67 grams of PO 94.4 grams of water 1798.0 grams of DPG 100.0 grams of supported perfluorosulfonic acid polymer Conditions:

50° C.

300 rpm 250 psig sample frequency was variable

The PO charge was injected into the reaction mixture, and a small exotherm, of 2° C., was observed for about 5 minutes. The reaction was continued for a total of 2 hours and 5 minutes of reaction time.

The data showed the PO conversion was 50% at 15 minutes into the experiment, and a final PO conversion of 90.9%. The reaction produced a final product having 4.3% TPG, 0.9% MPG, 0.4% TEPG, and 0.2% PEPG with the balance comprising DPG, water and byproducts. Undesirable byproducts concentration was determined to be in the range of 1.4% to 2.2%. The reduction in reaction temperature did reduce the production of dioxanes by approximately 50%.

The primary hydroxyl group content of the TPG produced was 29.90 percent.

Examples 11–17

These examples were performed using a 2 liter continuous stirred tank reactor system ("CSTR") with a mechanical agitator and a jacketed heating/cooling system. The reaction was uncatalyzed in a water environment up to about 19.9 moles water to mole of PO at water concentrations up to about 60 percent. In these experiments, the reactor was operated until steady state was reached. The results from Examples 11–17 were then utilized to study the kinetics of the reaction.

Example 11

Recipe:

333.4 grams of PO 1500.0 grams of water 1500.0 grams of DPG

Conditions:

150° C.

390 psig sample frequency=variable pump feed flowrate=32–34 mls/min

The CSTR reactor was operated at 150° C., and the recipe mixture pumped through the reactor at 32.8 mls/min. The reactor effluent contained 2.6% PO, 9.1% PG, 3.1% TPG, 0.2% TEPG, 0.07% PEPG, 0.007% byproducts with the balance being water and DPG. The PO yield to products was 91.4%, and the calculated PO molar mass balance was 102.9%, based on the analytical data.

Example 12

This example studies the effects of reduced water in the feed mixture.

Recipe:

300.0 grams of PO 750.0 grams of water 1950.0 grams of DPG

Conditions:

155° C.

390 psig sample frequency=variable pump feed flowrate=32–34 mls/min

At steady state, the reactor effluent contained 4.6% PO, 5.4% PG, 3.9% TPG, 0.2% TEPG, 0.05% PEPG, 0.0023% byproducts, with no balance of DPG and water.

As compared to Example 11, the TPG concentration in the reactor effluent increased by only 0.8%, from 3.1% to only 3.9% , even though there was a rather large change in the water concentration in the feed mix. The effects of excess water in the feed are nominal on the production of TPG, but affects the production of PG and DPG very significantly. PO conversion was only 45.9% and PO yield was 83.5%.

Example 13

This is an example of the CSTR operated at a higher reaction temperature.

Recipe:

300.0 grams of PO 750.0 grams of water 1950.0 grams of DPG

Conditions:

180° C.

390 psig sample frequency=variable pump feed flowrate=15–16 mls/min

At steady state the reactor effluent contained 1.3% PO, 8.8% PG, 6.7% TPG, 0.6% TEPG, 0.09% PEPG., 0.02% byproducts with a balance of DPG and water. Compared to Example 12, the TPG yield increased from 3.9% to 6.7% in response to the increase in reaction temperature and subsequently increased conversion of PO.

Example 14

This example was performed to more completely determine the effects of water on the reaction product distribution and the rate of conversion of PO, using a recipe with very high water concentration.

Recipe:

304.2 grams of PO 1800.4 grams of water 900.0 grams of DPG

Conditions:

155° C.

390 psig sample frequency=variable pump feed flowrate=15–16 mls/min agitator speed=500 rpm At steady state the reactor effluent contained 0.6% PO, 11.5% PG, 2.7% TPG, 0.2% TEPG, 0.05% PEPG, 0.079% byproducts and a balance of water and DPG. The PO conversion was 94.1%, and the calculated PO molar mass balance was 108.3%.

The data showed that a larger concentration of water dramatically reduces the production of TPG in favor of PG production.

The primary hydroxyl group content of the TPG produced was 28.2 percent.

Example 15

Recipe:

300.0 grams of PO 540.0 grams of water 2160.0 grams of DPG

Conditions:

155° C.

390 psig sample frequency=variable pump feed flowrate=15–16 mls/min agitator speed=500 rpm The reactor was operated in the same manner as in Example 14.

At steady state the data showed that the PO conversion was 58.5%, the PO yield was 69.7%, and the PO molar mass balance was 100.97%. The reactor effluent contained 4.2% PO, 6.1% PG, 4.7% TPG, 0.28% TEPG, 0.006% PEPG, 0.009% byproducts with a balance of water and DPG.

The reaction showed that low water concentration in the feed mixture improved the production of TPG, but the PO conversion decreased correspondingly.

The primary hydroxyl group content of the TPG produced was 25.33 percent.

Example 16

The reactor of Examples 11–15 was modified to accommodate the acid catalyzed process previously discussed, by addition of a separate metered feed system for the acid catalyst.

The modified reactor assembly further included a cross exchanger on the inlet of the reactor to preheat the incoming PO-water-DPG feed mix.

A pump, capable of 0.2 mls/min. to 10 mls/min. of flow, was used to pump the catalyst feed mixture to a mixing tee in front of the first preheater-cross exchanger, where the two feed components were partially mixed before heating. The first exchanger was a 2 feet length of ⅛" stainless steel tube inside a ¼" tube, with the hot reactor effluent flowing on the shell side. The second exchanger was constructed the same way, except that the length was 2.5 feet, the total length of cross exchanger needed to raise the feed mix temperature to 100° C.

The flow velocity through the preheater exchanger tubes provided some mixing of the reactants and catalyst solution prior to entry into the agitated reactor vessel.

Recipe:

801.5 grams of PO 921.5 grams of water 57.0 grams of DPG

Catalyst feed pump recipe:

3.78 grams of H3PO4 (85%) in 956.24 grams of water catalyst pump feed flowrate=2.0–2.1 mls/min Conditions:

155° C.

390 psig sample frequency=variable organic pump feed flowrate=30–32 mls/min agitator speed=500 rpm 100 mls of water containing 0.47 grams of H3PO4 pumped into the reactor to achieve a starting concentration of 200 ppm of H3PO4 catalyst prior to pumping the PO-water-DPG feed mixture into the reactor vessel. The two pump flows were calibrated and matched such that the catalyst feed pump would feed enough H3PO4 and water into the reactor to achieve the correct recipe composition and maintain 200 ppm of H3PO4 catalyst in the reactor at all times. The PO-water-DPG feed mix and the H3PO4-water catalyst mix were pumped to the reactor at 16 mls/min, total flow, to establish the ability of the cooling bath to handle the expected reaction exotherm. After two reactor volumes the feed flows to the reactor were slowly increased to 30.8 mls/min., including 2.0 mls/min. of catalyst feed mix.

At steady state a typical reactor effluent had the following composition; 0.35% P.O., 36.9% PG, 17.5% DPG, 5.9% TPG, 1.9% TEPG, 0.7% PEPG, 0.1% hexapropylene glycol ("HEXPG"), 0.03% byproducts with a balance of water.

The reactor residence time was 62 minutes, PO conversion was 98%, and the yield was 71.7%. The PO yield calculation formula does not include the DPG produced by the reaction.

The reaction product contained large concentrations of PG and DPG due to the presence of the water in the feed mixture.

The primary hydroxyl group content of the TPG produced was 42.9 percent.

Example 17

This example at higher reactants feed throughput, and lower reaction temperature, was performed to determine the limits of the modified reactor described in Example 16.

Recipe:

801.5 grams of PO 921.5 grams of water 57.0 grams of DPG

Catalyst feed pump recipe:

3.78 grams of H3PO4 (85%) in 956.2 grams of water catalyst pump feed flowrate=3.3–3.5 mls/min Conditions:

125° C.

390 psig sample frequency=variable organic pump feed flowrate=40–45 mls/min agitator speed=500 rpm The reaction was performed in the same manner as in Example 16.

At steady state the analytical results were as follows: 2.03% PO, 36.2% PG, 16.5% DPG, 5.4% TPG, 1.7% TEPG, 0.52% PEPG, 0.015% byproducts and the balance of water.

The primary hydroxyl group content of the TPG produced was 42.3 percent.

ANALYSIS OF EXAMPLES 11–17

Generally propylene glycol (PG) dipropylene glycol (DPG) and tripropylene glycol (TPG) are formed by reacting water and PO under neutral conditions as:

1. $PO+H_2O \rightarrow PG$
2. $PO+PG \rightarrow DPG$
3. $PO+DPG \rightarrow TPG$
4. $PO+TPG \rightarrow TET$
5. $PO+TET \rightarrow PENT$
6. $PO+PENT \rightarrow HEX$ Table 2 presents the portion of the data from Examples 11–17 used to evaluate water effect.

TABLE 2

EXPERIMENTAL DATA FOR CSTR* PROPYLENE GLYCOL REACTIONS

| | Temp | Res Time | Feed Comp, wt % | | | Product Comp. (normalized), wt % | | | | |
|---|---|---|---|---|---|---|---|---|---|---|
| EXAMPLE # | deg C. | min. | Water | PO | DPG | PO | PG | DPG | TPG | TET+ |
| 11 | 153.5 | 59 | 45 | 10 | 45 | 2.47 | 8.58 | 42.78 | 2.94 | 0.19 |
| 12 | 155.0 | 58 | 25 | 65 | 10 | 4.93 | 6.06 | 60.91 | 4.17 | 0.23 |
| 13 | 179.5 | 118 | 25 | 65 | 10 | 1.18 | 7.99 | 61.04 | 6.10 | 0.59 |
| 14 | 155.0 | 126.5 | 60 | 10 | 30 | 0.55 | 10.12 | 29.13 | 2.48 | 0.20 |
| 15 | 155.0 | 117.3 | 18 | 10 | 72 | 4.10 | 5.99 | 69.36 | 4.65 | 0.27 |
| 16 | 155.0 | 61.7 | 48.5 | 48.5 | 3 | 0.35 | 36.73 | 17.37 | 5.81 | 1.94 |
| 17 | 125.0 | 49 | 48.5 | 48.5 | 3 | 2.04 | 36.38 | 16.56 | 5.39 | 1.70 |

*Continuous Stirred Tank Reactor (or backmix reactor)

As stated above, Examples 11–17 were conducted in a 2000 ml CSTR. Temperature was controlled at the value shown. Samples were collected and analyzed until the reactor reached steady state. Data were normalized based on the effective PO content of the feed. The normalized product concentrations are shown in Table 2.

Adjustment factors, F1 and F2, were added to the reaction kinetics to account for the presence of the water as shown below:

1. rate 1=$k_1$[PO][WATER]* F1
2. rate 2=$k_2$[PO][PG]* F1
3. rate 3=$k_3$[PO][DPG]* F2
4. rate 4=$k_4$[PO][TPG]* F2
5. rate 5=$k_5$[PO][TET]* F2
6. rate 6=$k_6$[PO][PENT]* F2

The rate equations shown correspond to the reactions described earlier. The factors were split so that reactions 1 and 2 had a different correction factor than did reactions 3–6. Both F1 and F2 are functions only of the water concentration. F1 is applied to reacting hydroxyl species whose $pK_A$ is ~14, while F2 is applied to the weaker hydroxyls with a $pK_A$~16.

Using a simulator and the example results, F1 and F2 were varied to determine the best fit for each of the runs shown in Table 1. Appropriate values were selected based on how well the predicted TPG production matched lab data. Comparisons with PG and DPG production were also noted.

There are multiple combinations of F1 and F2 which will properly adjust the model to match an experimentally determined component concentration for a given water concentration. The (F1,F2) pairs were chosen to provide a smooth relationship between water concentration and the respective adjustment factor.

Figure 2:
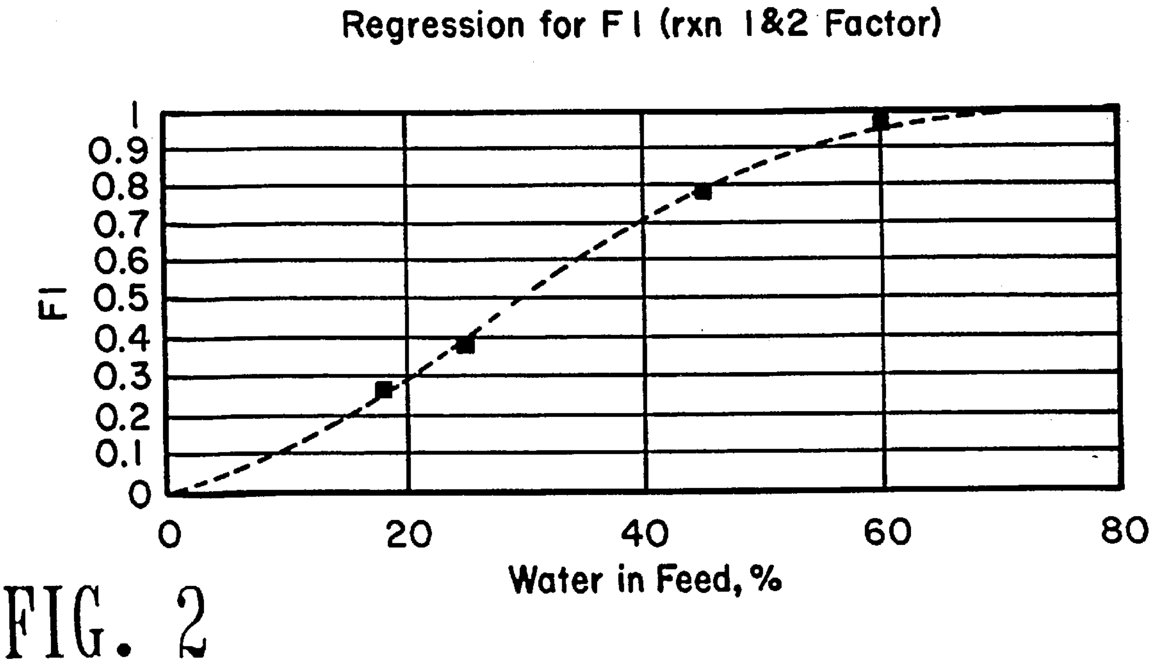
FIG. 2 is a plot of the water regression factor F1 plotted as a function of percent water in feed.

The values chosen for Examples 11 through 15 are presented in Table 3. The respective regression lines are shown in FIGS. 1 and 2.

TABLE 3

EXPERIMENTALLY DETERMINED F1 AND F2 VALUES

| Example # | Water, wt % | F1 | F2 |
|---|---|---|---|
| 15 | 18 | 0.26 | 0.062 |
| 12 | 25 | 0.37 | 0.12 |
| 11 | 45 | 0.78 | 0.28 |
| 14 | 60 | 0.96 | 0.47 |

The factors F1 and F2 were fit to a generalized sigmoid function of the form:

$$y=C+A/[B+\exp(-ax+b)]$$

End points used in the regression were:

| Water, # | F1 | F2 | |
|---|---|---|---|
| 0.01 | | 0.01 | 0.01 |
| 99 | 1. | 1. | |

Results of the regression are shown in Table 4.

TABLE 4

REGRESSED CONSTANTS FOR F1 AND F2 EQUATIONS

| | A | B | C | a | b |
|---|---|---|---|---|---|
| F1 | 0.287 | 0.262 | −0.079 | 0.08181 | 1.020 |
| F2 | 0.027 | −0.959 | −0.281 | 0.00096 | 0.525 |

Figure 3:
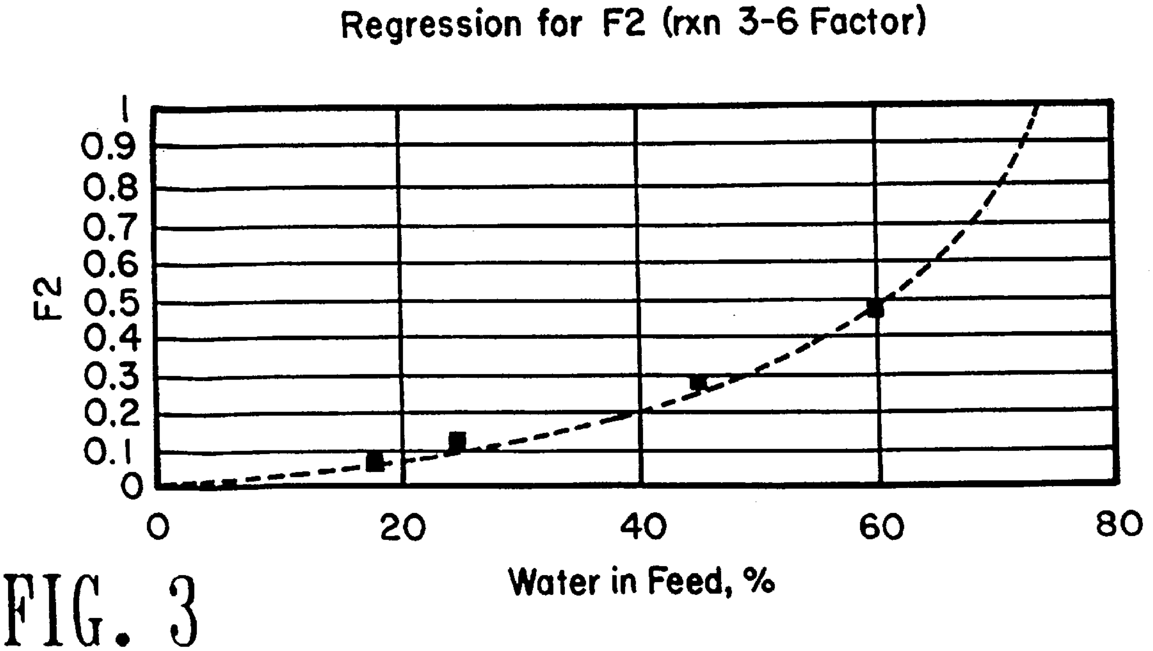
FIG. 3 is a plot of the water regression factor F2 plotted as a function of percent water in feed.

The data from Table 4 is shown plotted in FIGS. 2 and 3 which are plots of the water regression factors F1 and F2, respectively, plotted as a function of percent water in feed. Surprisingly, as the data shows, the addition of water to the system increases the reaction rates of all of the reactions.

Example 18

BUTYLENE OXIDE TO BUTYLENE GLYCOLS REACTION: (H3PO4 catalyzed)

A semi-batch reaction was performed in a 2 liter reactor vessel which contained 350 grams of water, 600 grams of monobutylene glycol and 2.35 grams of 85% phosphoric acid. The reactor and the mixture were heated to 155° C., with vigorous agitation. To this mixture, butylene oxide was added at the rate of 5 milliliters per minute. Fresh 85% phosphoric acid catalyst was injected into the reaction mixture at 45 minute intervals during 4.5 hours of butylene oxide addition. The reaction mixture was analyzed for residual butylene oxide at 1 hour intervals. The final reaction product contained no detectable butylene oxide. The product mixture contained 58% monobutylene glycol, 32% dibutylene glycol, 8% tributylene glycol and higher oligomers. The tributylene glycol primary hydroxyl content is 50%.

While the present invention is illustrated herein specifically for the reaction of an alkylene oxide with glycol, it is understood that the teachings of the present invention are believed to be equally applicable to reactions of alkylene oxide with alcohols in general, including mono-, di-, tri- and polyhydric alcohols, especially where it is desired to have a faster reaction rate and/or higher primary hydroxyl group content. Therefore, such reactions are intended to be within the scope of the disclosure of the present invention.

The description given herein is intended to illustrate the preferred embodiments of the present invention. It is possible for one of ordinary skill in the art to make various changes to the details of the present invention, without departing from the spirit of this invention. Therefore, it is intended that all such variations be included within the scope of the present invention as claimed.

We claim:

1. A trialkylene glycol composition in which greater than 36 percent of the hydroxyl groups are primary hydroxyl groups.

2. The trialkylene glycol composition of claim 1 in which the trialkylene glycol is tripropylene glycol or tributylene glycol and 40 percent of the hydroxyl groups are primary hydroxyl groups.

3. The trialkylene glycol composition of claim 1 in which the trialkylene glycol is tripropylene glycol or tributylene glycol and 44 percent of the hydroxyl groups are primary hydroxyl groups.

4. The trialkylene glycol composition of claim 1 in which the trialkylene glycol is tripropylene glycol or tributylene glycol and 48 percent of the hydroxyl groups are primary hydroxyl groups.

* * * * *

UNITED STATES PATENT AND TRADEMARK OFFICE

CERTIFICATE OF CORRECTION

PATENT NO. : 5,939,591

DATED : August 17, 1999

INVENTOR(S) : Jeffery David Birdwell, et al

It is certified that error appears in the above-identified patent and that said Letters Patent is hereby corrected as shown below:

Col. 1, Line 2, In the title, "GLYOCOLS" should read -- GLYCOLS --

Signed and Sealed this

Twenty-ninth Day of February, 2000

Attest:

Q. TODD DICKINSON

Attesting Officer

*Commissioner of Patents and Trademarks*